United States Patent [19]

Sheingorn

[11] Patent Number: 4,536,065
[45] Date of Patent: Aug. 20, 1985

[54] FIXATION DEVICE FOR EYE TESTING

[76] Inventor: Larry A. Sheingorn, 139 Lamont La., Gaithersburg, Md. 20878

[21] Appl. No.: 426,886

[22] Filed: Sep. 29, 1982

[51] Int. Cl.³ .............................................. A61B 3/02
[52] U.S. Cl. ..................................... 351/239; 351/244
[58] Field of Search ............... 351/224, 237, 243, 239, 351/240, 241, 223, 244

[56] References Cited

U.S. PATENT DOCUMENTS

| 1,610,517 | 12/1926 | Henry | 351/239 X |
| 3,883,234 | 12/1972 | Lynn et al. | 351/224 |
| 4,105,302 | 6/1976 | Tate, Jr. | 351/237 |
| 4,346,968 | 2/1980 | Melin et al. | 351/224 |
| 4,353,626 | 1/1980 | Harrison | 351/243 |
| 4,421,393 | 4/1981 | Cohen et al. | 351/224 |

Primary Examiner—Rodney B. Bovernick
Attorney, Agent, or Firm—Bacon & Thomas

[57] ABSTRACT

A fixation device having primary utility in testing children's eyes is disclosed. The device comprises employing remote control of a variety of fixation targets to maintain the attention of the child-patient.

6 Claims, 5 Drawing Figures

FIXATION DEVICE FOR EYE TESTING

BACKGROUND OF THE INVENTION

The present invention is directed to a fixation device for use in testing eyes, particularly children's eyes.

The use of accommodative targets is of unquestioned value in the evaluation of strabismus, a misalignment of the visual axes of the eyes. An accommodative target is a target which requires the patient to focus his or her eyes. A line of letters on a chart are accommodative targets, whereas light is a non-accommodative target.

In a co-operative adult, reading letters from a standard eye chart allows the opthalmologist to evaluate the alignment of the eyes. Children, however, are not as co-operative and either will not or cannot read letters from a chart. As a result, there are numerous devices that are intended to maintain a child's fixation at a distant point so that the alignment of the child's eyes can be examined.

One such device employs a film projector which projects a real image on the wall at the far end of the examination room. Appropriate images, such as animated cartoon characters, are used to interest the child and maintain fixation on the image.

There are, however, several technical problems with this device. First, the noise of the projector is often a distraction for the child. Second, the mechanical nature of the device makes it failure prone. More significantly, children generally view film in a passive, often disinterested manner, and as they become familiar with the cartoons that are inserted into the projectors their attention span is limited even on subsequent visits.

Other attempts to provide fixation devices for children have also exhibited limitations. One device consists of lights which are positioned so that when they are illuminated sequentially, they draw the patient's fixation to a central point. For example, lights positioned along the lines of an X can be illuminated to draw fixation toward the center of the X. Concentric circles can be illuminated in succession to draw attention to the center. Such devices, however, require co-operation from the patient and use a non-accommodative target, light. The non-accommodative target can seriously alter the strabismus evaluation.

Other fixation devices employ mechanical figures, e.g., dogs, clowns. When activated, the figures move, often make noise and provide, at least momentarily, an ideal fixation target. Unfortunately, as children become bored with the repetitive movements and sounds of the figures the fixation can be lost. To counteract this problem, a device employing numerous mechanical figures has been constructed. Each figure has its own source of illumination and when the child tires of one figure, the examiner simply turns it off and turns on another. Installation of this device, with all its interconnections, is a minor problem. More importantly, the examiner cannot devote his or her entire attention to evaluating the patient since the targets must be continually switched off and on.

SUMMARY OF THE INVENTION

My invention is intended to eliminate or minimize the problems associated with existing fixation devices. It is applicable to any one or more of the currently available fixation devices, although it is best used with numerous mechanical figures and light sources.

The fixation device of the invention is comprised of transmission means for transmitting any one of a plurality of characteristic signals selected by the operator to receiving means. The receiving means receives and identifies the characteristic signals and generates and directs a signal to appropriate function circuitry. The circuitry receives this signal and appropriately operates a plurality of fixation targets contained in a display panel in response thereto.

In an exemplary embodiment of my invention, the transmission means is a small radio transmitter mounted near the examiner, or wherever convenient, in a control unit. It is self-contained, preferably battery powered. The control unit contains keys or buttons for selecting a desired function. The receiving means is located at the far side of the examination room in a display panel which contains function circuitry and a plurality of fixation targets controlled by the function circuitry. Short-range transmitters and receivers are well known and are used in a variety of products such as remote controlled television sets and garage door openers, and need not be described further here.

In operation, a function is selected by the examiner by depressing a key on the control unit. This causes a signal which identifies the function to be transmitted by the transmitter to the receiver at the display panel. No physical connection is required between the examiner's control unit and the display panel containing the fixation targets.

The signal received by the receiver enables appropriate function circuitry via function command signals which then executes the function automatically. For example, when executing a sequential target activation function, the appropriate function circuitry sequentially turns one and only one fixation target on at a time. If the selected function is a sequential target activation with increasing duration function, a different function circuit is activated and sequentially turns one and only one fixation target on at a time while progressively increasing the time each new target is on. Similarly, a further function circuit can be provided which progressively shortens the time each target is turned on in sequence. Varying the time targets are on is helpful in maintaining the attention of children.

BRIEF DESCRIPTION OF THE FIGURES OF THE DRAWING

The figures of drawing provide further illustrations of exemplary embodiments of my invention.

DETAILED DESCRIPTION OF THE PREFERRED EMBODIMENTS

Figure 1:
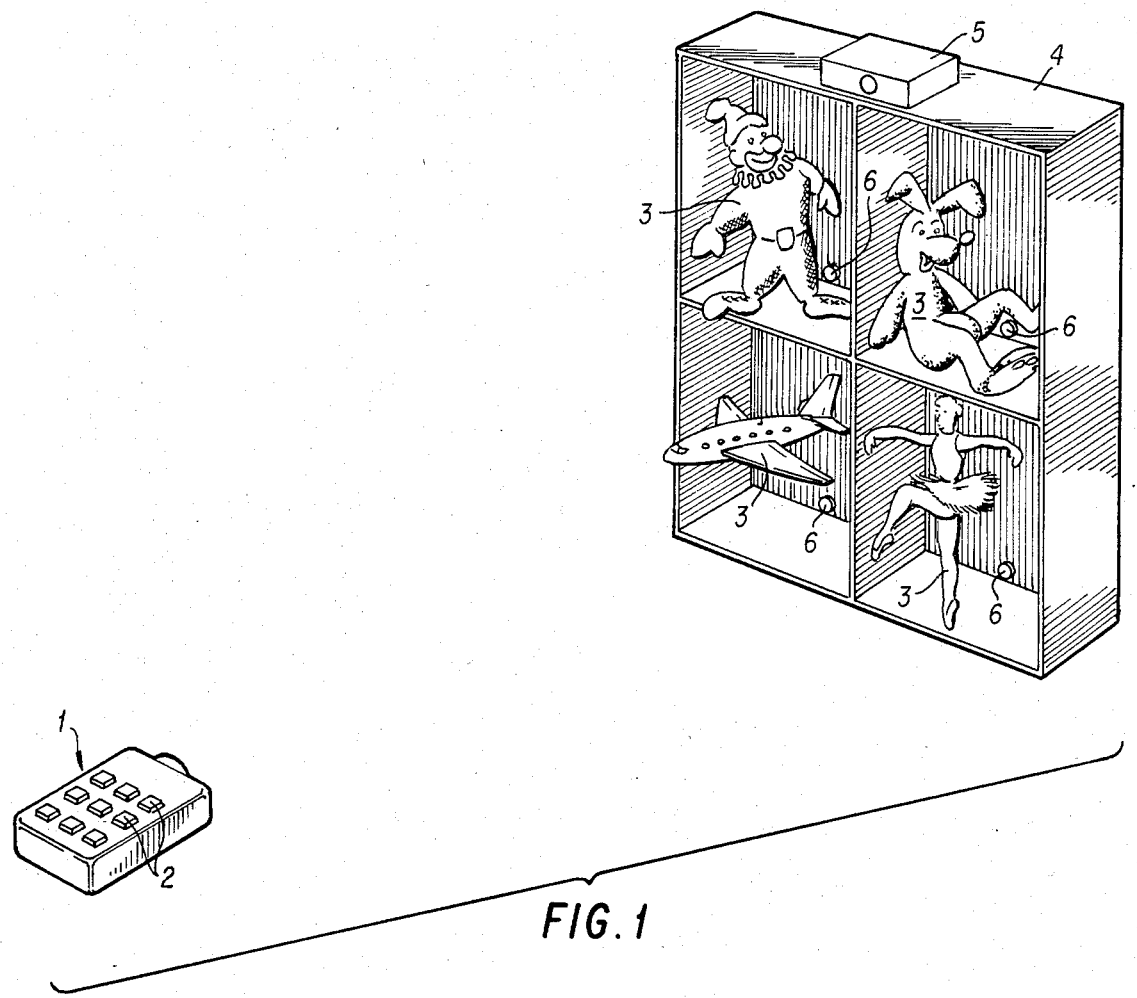
FIG. 1 depicts the control unit and display panel in accordance with the invention.

In FIG. 1, a fixation device designed in accordance with the invention is illustrated. The device comprises handheld control unit 1, which houses a small radio transmitter. Several keys 2 are provided to turn the transmitter on and generate a signal which is characteristic of a specific desired function. To minimize power requirements by the control unit, the transmitter is only activated during the time a key is depressed. Alternatively, a control unit can be housed in a floor unit which is controlled by the examiner's foot. This alternative leaves the examiner's hands free to work on the patient.

The fixation targets 3 are housed in display panel 4. Receiver 5 receives the signals transmitted from the control unit and selects the appropriate function circuitry which activates the fixation target(s) and, optionally, a corresponding light 6 to highlight the target. Because the device is particularly designed for testing children, fixation targets which attract the interest of a child should be selected. For example, toy animals or clowns which move and emit sounds when activated are appropriate.

Figure 2:
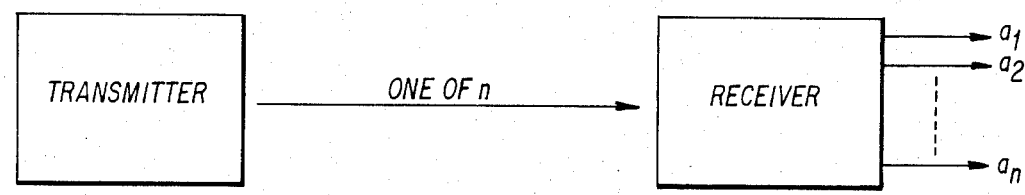
FIG. 2 is a block diagram illustrating the interrelation of the transmitter and receiver in accordance with the invention.

As shown in block in FIG. 2, the transmitter transmits any one of n signals to the receiver which receives and identifies the signal and activates the appropriate one of n function circuitry by generating command signals, $a_1$ $a_2$ . . . $a_n$, and directing them to the appropriate function circuitry. Two such function circuits are illustrated in FIGS. 3 and 4.

Figure 3:
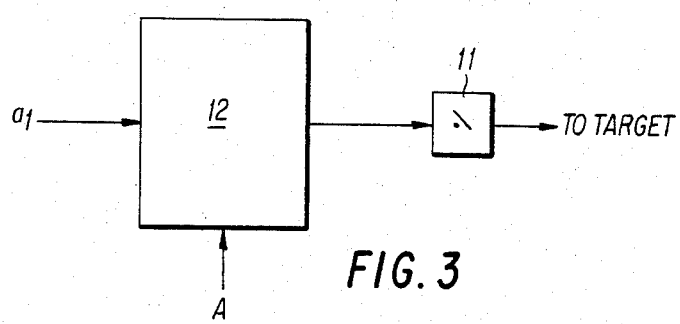
FIG. 3 shows on/off function circuitry in accordance with the invention.

The function circuitry of FIG. 3 activates one fixation target by closing electrical switch 11 in response to signal $a_1$ from the receiver. Flip-flop 12 is provided to disengage the switch upon receipt of reset signal A, which is generated each time any command signal is generated by the receiver. Generally, there will be one of these function circuits for each fixation target in the display panel, to permit the examiner to activate any one target of his or her choosing.

Figure 4:
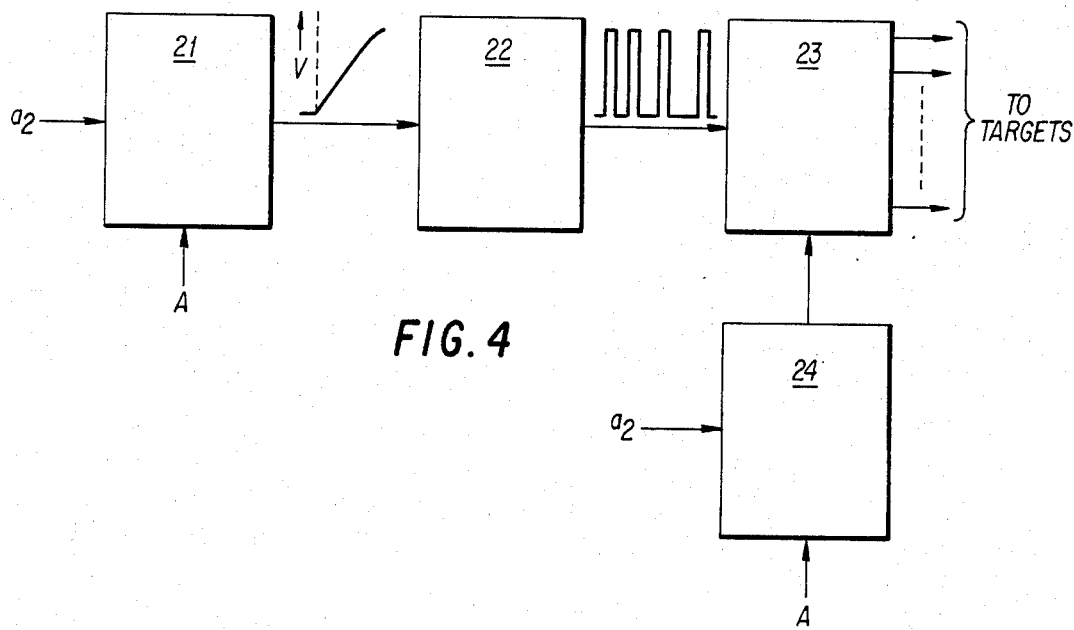
FIG. 4 depicts function circuitry for sequential target activation of increasing time duration in accordance with the invention.

FIG. 4 illustrates a function circuit for providing sequential target activation of progressively increasing duration. Signal $a_2$ is directed to the circuitry by the receiver and activates ramp generator 21, which generates a slowly increasing voltage. This voltage controls an oscillator 22, such that a square wave is produced, the frequency being inversely proportional to the control voltage. On the output of each pulse, counter 24 selects one of the fixation targets and activates it through an electrical switch. Flip-flop 23 is provided to enable the counter when the signal $a_2$ is received from the receiver and to cancel and reset the counter each time a command signal is generated by the receiver.

Figure 5:
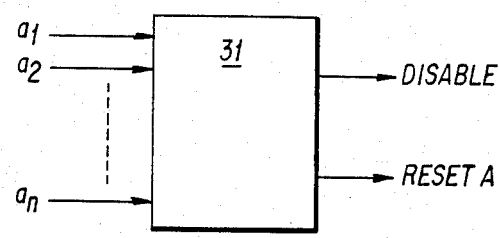
FIG. 5 shows circuitry which cancels an activated function upon receipt of a new function signal.

FIG. 5 shows the circuitry which resets all function circuits whenever a command signal is generated by the receiver. All command signals $a_1$ through $a_n$ are directed to gate 31 in addition to their respective function circuits. Each time a signal is received by gate 31, a disable and reset signal A is generated and directed to all function circuits. One command signal, $a_n$, does not control any function circuit and, therefore, disables all function circuits without enabling any other. This turns the device off.

Based upon the foregoing description, those of skill in the art will recognize that my invention provides a highly versatile fixation device. It can be used to mimic existing fixation devices by displaying a single fixation target or it can automatically present a series of targets in a variety of different sequences. It is particularly helpful in maintaining the attention of children.

While the invention has now been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

What is claimed is:

1. A fixation device for testing vision comprising:
   (a) remote transmission means for transmitting any one of a plurality of characteristic signals which is selected by the examiner,
   (b) receiving means having no physical connection to the transmission means for receiving and identifying said characteristic signal and for generating and directing a function command signal to the appropriate function circuitry, and
   (c) function circuitry for receiving the function command signals from the receiving means and operating two or more accommodative fixation targets in response thereto, wherein said accommodative fixation targets are mechanical figures which move and emit sounds when activated.

2. The device of claim 1, further comprising circuitry which disables and resets said function circuitry each time a function command signal is generated by said receiving means.

3. The device of claim 1, wherein said function circuitry operates said fixation targets by activating one and only one target in response to a function command signal.

4. The device of claim 1, wherein said function circuitry operates said fixation targets by activating a plurality of said targets in sequence in response to a function command signal.

5. The device of claim 4, wherein each target activated in sequence remains activated for a longer time than its predecessor.

6. The device of claim 1, wherein said fixation targets are illuminated by lights when activated.

* * * * *